United States Patent [19]
Westall

[11] 3,946,107
[45] Mar. 23, 1976

[54] INSECTICIDAL COMPOSITION OF BACILLUS THURINGIENSIS ADMIXED WITH PYRETHRUM

[75] Inventor: Edward B. Westall, San Jacinto, Calif.

[73] Assignee: Nutrilite Products, Inc., Buena Park, Calif.

[22] Filed: May 10, 1974

[21] Appl. No.: 468,865

[52] U.S. Cl. .................................. 424/93; 424/186
[51] Int. Cl.² .................... A01N 15/00; A01N 9/08
[58] Field of Search ............................. 424/93, 186

[56] References Cited
UNITED STATES PATENTS

| | | | |
|---|---|---|---|
| 3,063,893 | 11/1962 | Goldberg et al. | 424/186 |
| 3,150,062 | 9/1964 | Greenberg | 424/93 |

OTHER PUBLICATIONS
Chemical Abstracts, Vol. 79 (1973), p. 28409.

*Primary Examiner*—V. D. Turner
*Attorney, Agent, or Firm*—Burns, Doane, Swecker & Mathis

[57] ABSTRACT

An improved insecticidal composition is disclosed. *Bacillus thuringiensis*, Berliner is admixed with the natural botanical insecticide Pyrethrum in a ratio (by weight) of *Bacillus thuringiensis*, Berliner to Pyrethrum of from about 12 to 1 to about 1 to 20. The admixture preferably also contains a major amount of an inert carrier. The improved insecticide is particularly useful in the control of both sucking and chewing insects and larvae.

8 Claims, No Drawings

3,946,107

INSECTICIDAL COMPOSITION OF BACILLUS THURINGIENSIS ADMIXED WITH PYRETHRUM

BACKGROUND OF THE INVENTION

*Bacillus thuringiensis*, Berliner is well-known for use as a microbial insect pathogen useful against leaf-chewing insects such as the alfalfa caterpiller, the cosmopolitan green beetle, the European corn borer and Mediterranean flower moth. See, for example, U.S. Pat. 3,150,062. Although used for the toxic effects on general agricultural and forest leaf-chewing insect pests, *Bacillus thuringiensis*, Berliner has no substantial effect on sucking insects such as aphids and the like.

The search has continued for ways to increase the potency, toxicity and/or persistance of insecticides including *Bacillus thuringiensis*, Berliner. It has been proposed, for example, in Chemical Abstracts, 28409v, Vol. 79, p. 148 (1973) to mix *Bacillus thuringiensis* with equal amounts of a synthetic pyrethroid insecticide. Such mixtures, however, have been found undesirable since, for example, while *Bacillus thuringiensis* is exempt from tolerance levels, the synthetic pyrethroid insecticide is not and the resulting mixture containing a synthetic pyrethroid insecticide also is not exempt.

The search has continued for a more efficacious manner of utilizing *Bacillus thuringiensis*, Berliner as a general insecticide.

OBJECTS AND SUMMARY OF THE INVENTION

It is an object of this invention to substantially avoid or alleviate the problems of the prior art.

It is further an object of this invention to provide an improved *Bacillus thuringiensis*, Berliner-containing insecticide which has substantial potency.

It is also an object of this invention to provide a *Bacillus thuringiensis*, Berliner-containing insecticide which is useful against sucking insects as well as leaf-chewing insects.

In one aspect of the present invention there is provided an improved insecticidal composition comprising *Bacillus thuringiensis*, Berliner admixed with the natural botanical insecticide Pyrethrum in a weigth ratio of *Bacillus thuringiensis*, Berliner to Pyrethrum of from about 12 to 1 to about 1 to 20.

In another aspect of the present invention there is provided a method for the control of insects in an insect infested area which comprises applying to the said area an effective amount to control insects of the composition as above defined.

DETAILED DESCRIPTION OF THE INVENTION

*Bacillus thuringiensis*, Berliner is available in a form sufficient to be utilized as an insecticide in accordance with the present invention. It is preferred that the *Bacillus thuringiensis*, Berliner be produced by the process disclosed in U.S. Pat. 3,086,922 herein incorporated by reference. As disclosed therein, a microbial insecticide of high spore content and potency may be produced by the steps of (a) preparing an inoculant of the *Bacillus thuringiensis* microorganism to be utilized; (b) inoculation of a nutrient medium with the prepared inoculant; (c) propagation of the inoculated medium; (d) reducing the moisture content of the propagated medium to a proper low level; (e) commminuting the dried propagated medium and metabolic products to a particle size appropriate for utilization as an insecticide.

The nutrient medium may be absorbed onto a particulate inert inorganic carrier and nutrient substrate such as volcanic glasses (e.g., perlite and the like), exfoliated vermiculite, pumice, volcanic ash, calcined diatomaceous earth and similar materials. In this manner, as fully described and exemplified in the aforesaid U.S. Pat. 3,086,922, the microbial insecticide may be prepared in the form of a finely divided dry particulate material having a particle size such that essentially 100 percent of the particles pass through an 80 mesh (U.S. Standard Sieve) screen. Preferably, essentially all (i.e., 99 percent or more) of the particles pass through a 100 mesh screen. The potency of the microbial insecticide is at least about $1 \times 10^9$, generally at least $20 \times 10^9$, most preferably about $25 \times 10^9$, spores per gram.

Generally, the *Bacillus thuringiensis*, Berliner is present in admixture with Pyrethrum in a ratio (by weight) of *Bacillus thuringiensis*, Berliner to Pyrethrum of from about 12 to 1 to about 1 to 20, preferably from about 5 to 1 to about 1 to 6, most preferably from about 2 to 1 to about 1 to 2.

Pyrethrum is a commercially available botanical insecticide and may be used in its available form. As understood by those skilled in the art, commercial Pyrethrum comprises a mixture of four active insecticidal components, i.e., pyrethrin I and II and cinerin I and II.

Pyrethrum, for example, is available in the form of an oily liquid concentrate which may be adsorbed on or admixed with a suitable inert carrier such as bentonite, clay, talc, etc., having a particle size of from about +100 to −200 mesh (United States Sieve), preferably from about +150 to −200 mesh, most preferably from about +150 to about −175 mesh and containing from about 50 to 75, preferably from about 60 to 70, most preferably from about 65 to about 70, percent by weight of the Pyrethrum.

The *Bacillus thuringiensis*, Berliner-containing particles may be blended with sufficient Pyrethrum (preferably present also as particles of active material and inert carrier) to yield a mixture in the compositional amounts indicated above by suitable physical mixing techniques. Other suitable mixing techniques known to those skilled in the art may also be utilized.

The admixture of active materials (i.e., *Bacillus thuringiensis*, Berliner and Pyrethrum) and inert material generally contains from about 0.5 to about 8, preferably from about 1 to about 5.5, most preferably from about 2 to about 4, percent by weight of the admixture of active materials and concomitantly from about 92 to about 99.5, preferably from about 94.5 to about 99, most preferably from about 96 to about 98, percent by weight of the admixture of inert materials. In addition and if desired, the admixture may also contain minor amounts of other non-botanical active materials such as petroleum distillates which also function as carriers for the Pyrethrum.

It has been found that the blend of *Bacillus thuringiensis*, Berliner and Pyrethrum not only has a more toxic effect than would be expected from the utilization of either of these materials alone but also has a broader spectrum of use. That is, while *Bacillus thuringiensis*, Berliner is generally used against leaf-chewing insects the *Bacillus thuringiensis* - Pyrethrum mixture also shows considerable effectiveness against sucking insects and a higher toxicity for leaf chewing ensects than expected from the Pyrethrum alone.

The improved insecticidal composition of the present invention is advantageously adapted to be packaged, handled and disseminated. In the ultimate use of the insecticidal compositions of the present invention into insect infested areas, any conventional application technique may be utilized. For example, the compositions and particularly when included with inert carrier materials are well suited for efficient and accurate application to insect infested areas from airplanes. The particles may also be dispersed in an aqueous solution and agitated and sprayed into the insect infested areas.

Although the amount of active material will vary depending upon the insect to be controlled, generally the insecticidal compositions of the present invention will be utilized in an amount of from about 0.05 to about 0.75, preferably from about 0.10 to about 0.50, most preferably from about 0.10 to about 0.33, pounds of active material per acre of treated area.

As noted above, the improved insecticidal compositions of the present invention may be utilized for the treatment and control both of leaf-chewing insect pests (European corn borer, alfalfa caterpiller, cosmopolitan green beetle, Mediterranean flower moth cabbage looper, imported cabbage worm, leaf roller, leaf tier, hornworm or the like) and also of sucking insect pests (aphids, leaf hopper, thrip, flea beetle, cucumber beetle and the like).

Both the natural Pyrethrum botanical insecticide as well as the *Bacillus thuringiensis*, Berliner are exempt from tolerance levels when used according to label directions, and the resulting *Bacillus thuringiensis* Berliner - Pyrethrum mixture is exempt from tolerance levels when used according to label directions.

The invention is additionally illustrated in connection with the following Examples which are to be considered as illustrative of the present invention. It should be understood, however, that the invention is not limited to the specific details of the Examples.

EXAMPLE I

*Bacillus thuringiensis*, Berliner is made in the manner of Example VI of U.S. Pat. 3,086,922. The prepared *Bacillus thuringiensis*, Berliner material contains about 13 percent by weight active material on 98.7 percent by weight of growth media as an inert carrier comminuted to 100 percent minus 80 mesh and has a viable spore count of $25 \times 10^9$ spores per gram. All toxicities are given in terms of the $LD_{50}$ rate and in terms of International Units (IU). As understood by those skilled in the art, International Units are a measure of larval toxicity and the $LD_{50}$ level is the amount of material required to kill 50 percent of a larvae.

The Pyrethrum particles are prepared by contacting a 20 weight percent solution of commercially available Pyrethrum with Bentonite particles and drying the resulting particles. These prepared particles contain about 50 weight percent Pyrethrum Concentrate and 50 weight percent Bentonite.

A portion of each of the *Bacillus thuringiensis*, Berliner-containing particles and the Pyrethrum-containing particles are admixed to form an insecticidal admixture containing the *Bacillus thuringiensis*, Berliner and Pyrethrum present in ratios (by weight) of 2:1, 1:1 and 1:2. The total amount of active material (i.e., *Bacillus thuringiensis*, Berliner and Pyrethrum) in each admixture is 2, 3, and 4, weight percent of the total admixture, respectively.

The $LD_{50}$ rates of the individual materials and of the mixtures in a test run on Cabbage Looper are shown below in Table I.

Table I

| | *Bacillus thuringiensis*, Berliner | Pyrethrum | Weight Ratio, *Bacillus thuringiensis*, Berliner to Pyrethrum in admixture 1%–1/2% | 1/2%–1% | 1%–2% |
|---|---|---|---|---|---|
| $LD_{50}$, IU | 1500 | 1500 | 3560 | 4840 | 5800 |

It may be seen that the mixture of Pyrethrum and *Bacillus thuringiensis*, Berliner has a significantly higher toxicity than the individual components and much higher than would be expected from a mixture.

EXAMPLE II

A number of plots containing both chewing insect pests (e.g., Cabbage Looper) and sucking insect pests (e.g., Aphids) are contacted with the *Bacillus thuringiensis*, Berliner-containing particles made as in Example I and the *Bacillus thuringiensis*, Berliner - Pyrethrum admixture of Example I. Each of these materials is applied in the same manner and at the same rate (i.e., 3 pounds of active material per acre). These plots are surveyed before and after application of these materials to determine the percent mortality of the insect pests. The results are shown below in Table II.

Table II

Insect Mortality by Treatment

| Insect Pest | *Bacillus thuringiensis*, Berliner | Pyrethrum | *Bacillus thuringiensis*, Berliner - Pyrethrum admixture |
|---|---|---|---|
| Leaf Chewing | 65% | 10% | 100 |
| Sucking | 0% | 85% | 85% |

Again, the surprising toxicity and scope of use of the insecticidal composition of the present invention is apparent.

The principles, preferred embodiments and modes of operation of the present invention have been described in the foregoing specification. The invention is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. An improved insecticidal composition comprising *Bacillus thuringiensis*, Berliner admixed with the natural botanical insecticide Pyrethrum in a weight ratio of *Bacillus thuringiensis*, Berliner to Pyrethrum of from about 2 to 1 to about 1 to 2.

2. The improved insecticidal composition of claim 1 wherein said admixture further contains an inert carrier.

3. The improved insecticidal composition of claim 2 wherein said insecticidal composition contains from about 92 to about 99.5 weight percent of the total composition of said inert carrier.

4. The improved insecticidal composition of claim 1 wherein said admixture further contains an inert carrier in an amount of from about 94.5 to about 99 weight percent of the total composition.

5. The improved insecticidal composition of claim 4 wherein said admixture further contains an inert carrier in an amount of from about 96 to about 98 weight percent of the total composition.

6. A method for the control of insects in insect infested areas which comprises applying to said insect infested areas an effective amount of the insecticidal composition of claim 1.

7. The method of claim 6 wherein the composition applied further contains an inert carrier in an amount of from about 94.5 to about 99 weight percent of the total composition.

8. The method of claim 6 wherein the composition applied further contains an inert carrier in an amount of from about 96 to about 98 weight percent of the total composition.

* * * * *